US008346364B2

(12) United States Patent
Sueda

(10) Patent No.: US 8,346,364 B2
(45) Date of Patent: Jan. 1, 2013

(54) EVOKED SPINAL CORD POTENTIAL MONITORING APPARATUS AND EVOKED SPINAL CORD POTENTIAL MONITORING SYSTEM

(75) Inventor: Taijiro Sueda, Hiroshima (JP)

(73) Assignee: Hiroshima University, Hiroshima (JP)

( * ) Notice: Subject to any disclaimer, the term of this patent is extended or adjusted under 35 U.S.C. 154(b) by 362 days.

(21) Appl. No.: 12/515,102

(22) PCT Filed: Jun. 25, 2007

(86) PCT No.: PCT/JP2007/062732
§ 371 (c)(1),
(2), (4) Date: Aug. 10, 2009

(87) PCT Pub. No.: WO2008/059634
PCT Pub. Date: May 22, 2008

(65) Prior Publication Data
US 2010/0030309 A1    Feb. 4, 2010

(30) Foreign Application Priority Data

Nov. 16, 2006 (JP) .................................. 2006-310814

(51) Int. Cl.
*A61N 1/00* (2006.01)
(52) U.S. Cl. .......................................... 607/40; 607/117
(58) Field of Classification Search .................... 607/40, 607/117
See application file for complete search history.

(56) References Cited

U.S. PATENT DOCUMENTS 6,308,105 B1 * 10/2001 Duysens et al. .............. 607/118
6,600,956 B2 * 7/2003 Maschino et al. ............ 607/118

FOREIGN PATENT DOCUMENTS

JP    60-194933    10/1985
JP    2006-187342    7/2006

OTHER PUBLICATIONS

Kumagai et al., "Evoked Spinal Cord Potentials Monitored at Thoracoabdominal Region after Trans-intercostal Stimulation," *Hiroshima Journal of Medical Science*, 55(2):53-57 (2006).
PCT; International Search Report dated Jul. 25, 2007 in Application No. PCT/JP2007/062732.
PCT; Written Opinion dated Jul. 25, 2007 in Application No. PCT/JP2007/062732.
PCT; International Preliminary Report on Patentability dated May 19, 2009 in Application No. PCT/JP2007/062732.

* cited by examiner

*Primary Examiner* — Niketa Patel
*Assistant Examiner* — Alyssa M Alter
(74) *Attorney, Agent, or Firm* — Snell & Wilmer L.L.P.

(57) ABSTRACT

The evoked spinal cord potential monitoring apparatus of the present invention includes: a pair of electrodes 14; and a holding section 12 for holding the pair of electrodes 14, a tip section of each of the electrodes 14 being extended outwards from an end of the holding section 12, and the electrodes 14 being movable relative to the holding section 12. A hook section 15 engageable to an intercostal nerve is provided at the tip section of each of the electrodes 14, and the electrodes 14 or the holding section 12 is moved while the hook section 15 is coupled to the intercostal nerve such that the hook section 15 and the holding section 12 are able to hold the intercostal nerve therebetween. The apparatus requires no preoperative preparation, is capable of coping with an emergency case, and further, is unsusceptible to the influence of anesthetics.

6 Claims, 8 Drawing Sheets

EVOKED SPINAL CORD POTENTIAL MONITORING APPARATUS AND EVOKED SPINAL CORD POTENTIAL MONITORING SYSTEM

TECHNICAL FIELD

The present invention relates to an evoked spinal cord potential monitoring system by intercostal nerve stimulation—recording, and to an evoked spinal cord potential monitoring apparatus used for the evoked spinal cord potential monitoring system.

BACKGROUND ART

Paraplegia (paralysis of the lower part of the body) resulting from spinal cord ischemia during an operation, such as thoracoabdominal aorta operation, thoracic descending aortic aneurysm operation and spinal cord injury operation, is a complication that significantly damages the quality of life (QOL) of a patient.

Various methods for protecting the spinal cord have been developed until now; however, such methods have not achieved complete prevention of paraplegia.

A method utilizing evoked spinal cord potentials can be recognized as a method for monitoring paraplegia during an operation. The said method is for recording, as electromagnetic waveforms, current running through the spinal cord caused by electric stimulation, and observing changes, such as an amplitude drop of the waveforms, when the spinal cord is experiencing ischemia and the conduction of the electricity becomes poor.

Conventionally, a stimulating electrode is placed at the scalp or the periphery of the cervical spinal cord dura mater to obtain waveforms from a recording electrode placed at a periphery of the thoracolumber dura mater or a muscle of the leg.

However, such a conventional evoked spinal cord potential monitoring method has various problems as follows: (1) when inserting an electrode into the periphery of the dura mater, it is necessary to insert and place the electrode at the periphery of the dura mater on the prior day of the operation in order to avoid a complication of bleeding because heparin is used during the operation; (2) the electrode cannot be used for an emergency operation; and (3) in a case where the potential is recorded from a muscle of the leg, the potential cannot be recorded if a muscle relaxant is used during the surgery.

Due to the drawbacks described above, narcoses and potential monitoring methods face significant difficulties.

DISCLOSURE OF THE INVENTION

The present invention is intended to solve the drawbacks described above. The objective of the present invention is to provide an evoked spinal cord potential monitoring system that requires no preoperative preparation, is capable of coping with an emergency case, and further, is unsusceptible to the influence of anesthetics; and an evoked spinal cord potential monitoring apparatus used for the evoked spinal cord potential monitoring system.

An evoked spinal cord potential monitoring apparatus according to the present invention includes: a pair of electrodes; and a holding section for holding the pair of electrodes, a tip section of each of the electrodes being extended outwards from an end of the holding section, and the electrodes being movable relative to the holding section, wherein a hook section engageable to an intercostal nerve is provided at the tip section of each of the electrodes, and the electrodes or the holding section is moved while the hook section is engaged to the intercostal nerve such that the hook section and the holding section are able to hold the intercostal nerve therebetween, thereby achieving the objective described above.

In one embodiment of an evoked spinal cord potential monitoring apparatus according to the present invention, the holding section is a case, and the pair of the electrodes are positioned in the case such that the pair of the electrodes are extendable out of and retractable in the case; an elastic body is provided between each of the electrodes and the case to retract the pair of electrodes in the case; and the hook sections of the electrodes and a tip section of the case are able to hold the intercostal nerve therebetween.

In one embodiment of an evoked spinal cord potential monitoring apparatus according to the present invention, the case includes therein an electric connection section to the electrodes.

In one embodiment of an evoked spinal cord potential monitoring apparatus according to the present invention, the electric connection section includes a stereo jack and an electrode cable for connecting the stereo jack and the electrodes.

In one embodiment of an evoked spinal cord potential monitoring apparatus according to the present invention, the holding section includes a fixed prong which is thrustable into tissues.

In one embodiment of an evoked spinal cord potential monitoring apparatus according to the present invention, the holding section is a tubular body for housing the electrodes and a pair of electrodes are positioned in the tubular body such that the pair of electrodes are movable in an axis direction of the tubular body; and a support section for supporting the electrodes is fit with the tubular body, and an elastic body is provided between the tubular body and the support section, the elastic body biasing each of the electrodes to be retracted in the tubular body.

In one embodiment of an evoked spinal cord potential monitoring apparatus according to the present invention, the holding section is a tube covering the electrodes, the tube being configured to be movable in an axis direction of the electrodes; a support section for supporting the electrodes is movably fit with the tube; and a spring is provided between the support section and the tube, the spring biasing the tube in a direction towards the hook section of the electrodes.

In one embodiment of an evoked spinal cord potential monitoring apparatus according to the present invention, each of the electrodes is covered by the tube and the pair of the electrodes are connected to each other by a connecting member.

In one embodiment of an evoked spinal cord potential monitoring apparatus according to the present invention, a space between the pair of the electrodes is 2 to 3 mm.

An evoked spinal cord potential monitoring system according to the present invention for monitoring spinal cord ischemia during an operation includes evoked spinal cord potential monitoring apparatuses attached respectively to exposed upper and lower intercostal nerves, where each of the evoked spinal cord potential monitoring apparatuses includes a pair of electrodes; and a holding section for holding the pair of electrodes, a tip section of each of the electrodes being extended outwards from an end of the holding section, and the electrodes being movable relative to the holding section; and a hook section engageable to an intercostal nerve is provided at the tip section of each of the electrodes, and the electrodes or the holding section is moved while the hook section is engaged to the intercostal nerve such that the hook section and the holding section are able to hold the intercostal nerve therebetween, thereby achieving the objective described above.

In one embodiment of an evoked spinal cord potential monitoring system according to the present invention, the holding section is a case, and the pair of the electrodes are positioned in the case such that the pair of the electrodes are extendable out of and retractable in the case; a spring is provided between each of the electrodes and the case to retract the pair of electrodes in the case; and the hook sections of the electrodes and a tip section of the holding section are able to hold the intercostal nerve therebetween.

In one embodiment of an evoked spinal cord potential monitoring system according to the present invention, the evoked spinal cord potential monitoring apparatus attached to the upper intercostal nerve is connected with an electric stimulation section, and the evoked spinal cord potential monitoring apparatus attached to the lower intercostal nerve is connected with a recording section for recording electric signals conducted from the spinal cord to the lower intercostal nerve as waveforms.

In one embodiment of an evoked spinal cord potential monitoring system according to the present invention, the holding section includes therein an electric connection section to the electrodes.

In one embodiment of an evoked spinal cord potential monitoring system according to the present invention, the electric connection section includes: a stereo jack, and an electrode cable for connecting the stereo jack and the electrodes.

An evoked spinal cord potential monitoring system according to the present invention for monitoring spinal cord ischemia includes evoked spinal cord potential monitoring apparatuses attached respectively to exposed upper and lower intercostal nerves of an aorta intercepted during an operation, where each of the evoked spinal cord potential monitoring apparatuses includes a pair of electrodes; and a holding section for holding the pair of electrodes, a tip section of each of the electrodes being extended outwards from an end of the holding section, and the electrodes being movable relative to the holding section; and a hook section engageable to an intercostal nerve is provided at the tip section of each of the electrodes, and the electrodes or the holding section is moved while the hook section is coupled to the intercostal nerve such that the hook section and the holding section are able to hold the intercostal nerve therebetween, thereby achieving the objective described above.

According to the evoked spinal cord potential monitoring apparatus of the present invention, a hook section is provided at a tip section of each of electrodes, the hook section being capable of coupling to an intercostal nerve. It is possible to hold the intercostal nerve in between the hook section and a holding section by moving the electrodes or the holding section while the hook section maintains to couple to the intercostal nerve.

Therefore, the electrodes are moved from the holding section, and the hook section formed at the tip section of each of the electrodes is extended out of the holding section. The hook section is coupled to the intercostal nerve. While maintaining that state, the electrodes are moved towards the holding section side (or the holding section is moved while the hook section is maintained to be coupled to the intercostal nerve), so that the intercostal nerve is held between the hook section and the holding section. As a result, the electrodes can be in contact with the intercostal nerve in a secure and stable manner.

As described above, the electrodes of the evoked spinal cord potential monitoring apparatus are attached to the respective exposed intercostal nerves in the upper and lower parts of the aorta, which is intercepted during the operation. Accordingly, the upper intercostal nerve is electrically stimulated by the evoked spinal cord potential monitoring apparatus attached to the upper intercostal nerve, and electric signals conducted from the spinal cord to the lower intercostal nerve are recorded as waveforms by the evoked spinal cord potential monitoring apparatus attached to the lower intercostal nerve.

Accordingly, utilizing the evoked spinal cord potential monitoring system of intercostal nerve stimulation, it is possible to obtain intercostal nerve recording, so that the system requires no preoperative preparation, is capable of coping with an emergency case, and further, is unsusceptible to the influence of anesthetics.

An electric connection section (e.g., stereo jack and electrode cable) to each electrode is provided to a case, so that the electrodes can be easily extended out of or retracted in the case, and further, the manufacturing of the monitoring apparatus is facilitated.

According to the evoked spinal cord potential monitoring system of the present invention for monitoring spinal cord ischemia during an operation, evoked spinal cord potential monitoring apparatuses are provided, each of which is attached to the upper and lower parts of the exposed intercostal nerves respectively, so that the upper intercostal nerve is electrically stimulated by the evoked spinal cord potential monitoring apparatus attached to the upper intercostal nerve, and electric signals conducted from the spinal cord to the lower intercostal nerve are recorded as waveforms by the evoked spinal cord potential monitoring apparatus attached to the lower intercostal nerve. Herein, the evoked spinal cord potential monitoring apparatus includes the configuration described above, so that the electrodes can be in contact with the intercostal nerve in a secure and stable manner. In addition, it becomes possible to evaluate the function of the spinal cord as a neural transmission path in detail, and to have an accurate grasp of the location of the spinal cord where ischemia or damage is occurred.

The applicant of the patent has already used this method in an experiment using animals and has demonstrated its effectiveness.

The evoked spinal cord potential monitoring apparatus according to the present invention can be used in the field of operations and can be applied for a case of an emergency operation. Further, the evoked spinal cord potential monitoring apparatus has little influence due to anesthetics, such as muscle relaxant, and can perform the monitoring of the spinal cord corresponding to the location of the aorta to be operated, which makes it even possible to perform a localized diagnosis of the spinal cord ischemia.

Furthermore, according to the evoked spinal cord potential monitoring by the evoked spinal cord potential monitoring apparatus, the detected results are successively analyzed, so that the function of the spinal cord as a neural transmission path can be evaluated in detail, and further, it becomes possible to have an accurate grasp of the location of the spinal cord where ischemia or an damage is occurred.

Furthermore, by using the stimulating and recording electrodes for the intercostal nerve, which are required for performing the present method, it becomes possible to effectively perform the stimulating and recording without damaging the intercostal nerve. This is because the method using the electrodes records, as electromagnetic waveforms, current running through the spinal cord caused by electric stimulation, and observes changes, such as an amplitude drop of the waveforms, when the spinal cord is experiencing ischemia and the conduction of the electricity becomes poor. Further, when the electrodes are small in size, light in weight and flexible as evoked spinal cord potential monitoring electrodes, the electrodes can be suitably placed directly onto a surface of the nerve with an appropriate pressure without damaging the nerve.

Other than the monitoring of the spinal cord ischemia during the thoracoabdominal aorta operation, thoracic descending aortic aneurysm operation and spinal cord injury operation, the present invention can be applied for a diagnosis of the spinal cord damage, including the damage of the spinal cord due to a traffic accident, an accidental fall from a high position, stumbling, blow, being buried under a collapsed object, the deformity of the spinal cord, a tumor of the spinal cord, and the like.

Further, the trans-intercostal evoked spinal cord potential (Tic-ESCP) is monitored. Therefore, firstly, it is unsusceptible to the influence of external noise since the waveforms of the Tic-ESCP are simple and reflect the activation along short segments of the spinal cord. Secondly, a preoperational preparation, such as placing the electrodes in the periphery of a dura mater, is not required, so that the present invention is available not only for an emergency case but also for a patient who is under an anti-blood coagulation treatment or an anti-platelet treatment. Thirdly, it is allowed to use a muscle relaxant, so that nerve potentials can be evaluated without the disturbance of the muscle. Although the electrodes are small, the waveforms are simple and clear, and therefore, it is easy to analyze the waveforms. Fourthly, stimulation is provided directly to the nerve, thus a smaller stimulation is required.

Particularly, a fixed prong thrustable into tissues is provided for the holding section, so that the fixed prong can be thrust into tissues to fix the holding section at any tissue location.

The holding section can be formed as a case. In such a case, a pair of electrodes positioned in the case are extendable out of and retractable in to(movable in the front and back directions) the case. Therefore, the electrodes are slidably extended out of the case and the hook section provided at the tip section of each of the electrodes is coupled to the intercostal nerve, and the electrodes are moved into the case while maintaining the state. As a result, the electrodes can be in contact with the intercostal nerve in a secure and stable manner.

Figure 1:
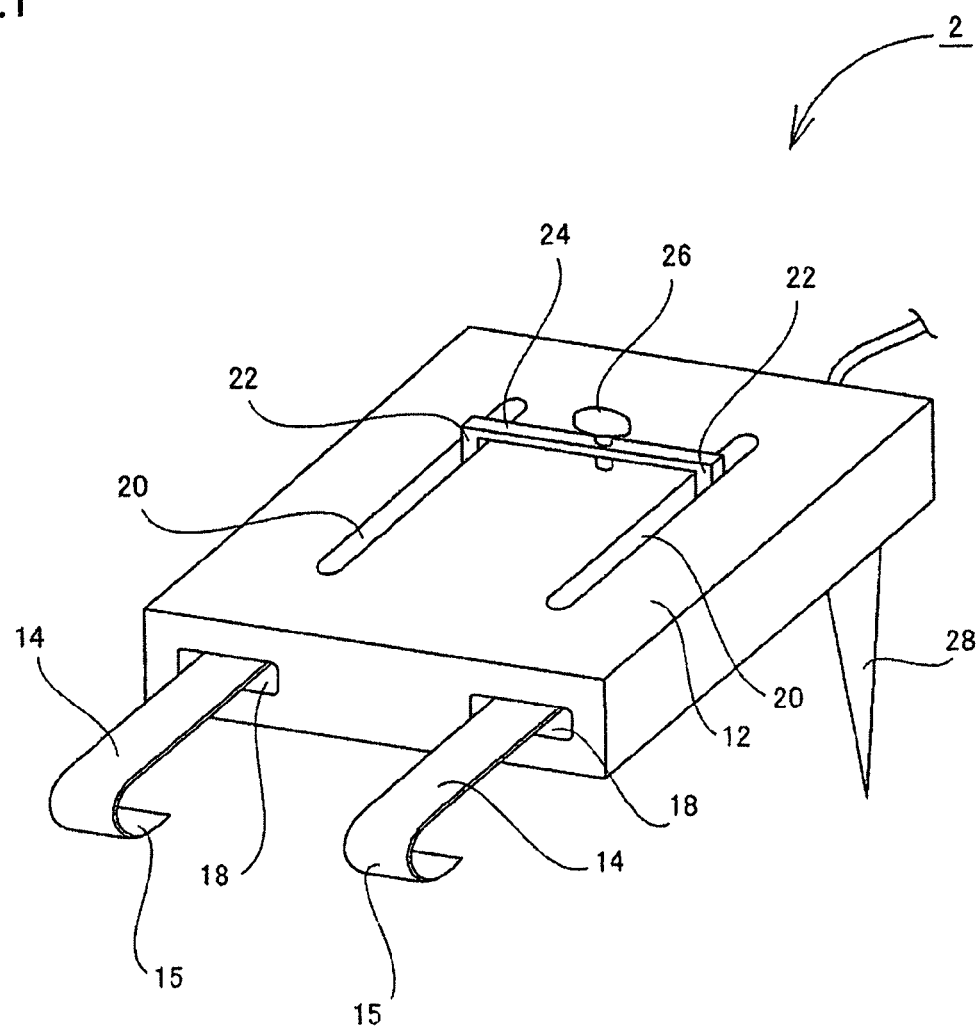
FIG. 1 is a perspective view of an evoked spinal cord potential monitoring apparatus according to one embodiment of the present invention.

2 evoked spinal cord potential monitoring apparatus
12 case
14 electrode
15 hook section
16 fixing section
18 opening section
27 spring
28 fixing prong

BEST MODE FOR CARRYING OUT THE INVENTION

Embodiments of the present invention will be described based on the accompanying figures.

As illustrated in FIGS. 1 to 5, an evoked spinal cord potential monitoring apparatus 2 includes: a case 12 as a holding section; a pair of electrodes 14 positioned in such a manner to be extendable out of and retractable into the case 12; a fixing section 26 capable of fixing both of the electrodes 14 to the case 12 such that the electrodes are extended out of an opening 18 in the case 12.

The case 12 is formed in a flat box shape with electrically insulated resin and the like, and each of the electrodes 14 are positioned on either side of the case 12.

The opening 18 is provided at the front end of the case 12, and each tip section of the electrodes 14 are extendable in a forward direction from the opening 18, the tip section being positioned within a housing section of the case 12. Both of the electrodes 14 are configured to be slidable so as to be extended in a forward direction from the housing section through the opening 18 or retracted to be housed in the case 12.

Although the shape of the electrodes 14 are not limited as long as they are in a shape that does not damage the intercostal nerve, the electrodes 14 are formed with a belt shaped conductive metal piece in this embodiment as illustrated in FIG. 1.

Conventionally known materials can be used as a material for the electrodes, such as platinum, silver, copper, stainless steel, gold, and a conductor coated with gold. Particularly, gold and materials coated with gold are preferable. The thickness of the electrodes 14 are preferably 0.8 mm to 1.2 mm.

In addition, conductive polymer can be used as a material for the electrodes 14. Such a conductive polymer includes, for example, polyacetylene, polypyrrole, polythiophene, poly-p-phynylene, polyphenylenevinylene and the like.

The space between a pair of electrodes 14 is preferably set to be 2 mm to 3 mm in terms of the stability of the potential difference.

Optionally, the electrodes 14 maybe in a wire shape. It is preferable that the electrodes 14 have elasticity to some extent. The opening 18 described above may be formed along the entire width of the case 12.

A hook section 15 is formed at the tip section of each of the electrodes 14, the hook section being curved downwards. The hook section 15 is defined to have a shape that is capable of being coupled to the intercostal nerve. The shape of the hook section 15 may be a half circle shape in a side view.

Long apertures 20 are formed on the upper surface of the case 12, the long apertures 20 extending in front and back directions; and an electrode lever 22 connected to each electrode 14 protrudes outwards through each long aperture 20. Both of the electrode levers 22 are connected to each other by an electrically insulated connecting member 24.

When the connecting member 24 is operated to move in front and back directions of the case 12 by hand and the like, both of the electrodes 14 are slidably moved in front and back directions within the case 12. The connecting member 24 includes a screw 26 as a fixing section attached thereto. By turning the screw 26 by hand, the connecting member 24 can be fixed to the case 12, and by loosening the screw 26, the connecting member 24 and electrodes 14 can be moved in front and back directions of the case 12 along the long apertures 20.

The case 12 includes a pair of fixing prongs 28 provided on the left and right in back of the lower surface of the case 12, the fixing prongs being thrustable into tissues. By thrusting the fixing prong 28 into any point of the tissues, the case 12 can be fixed to a desired position of the tissues.

Figure 2:
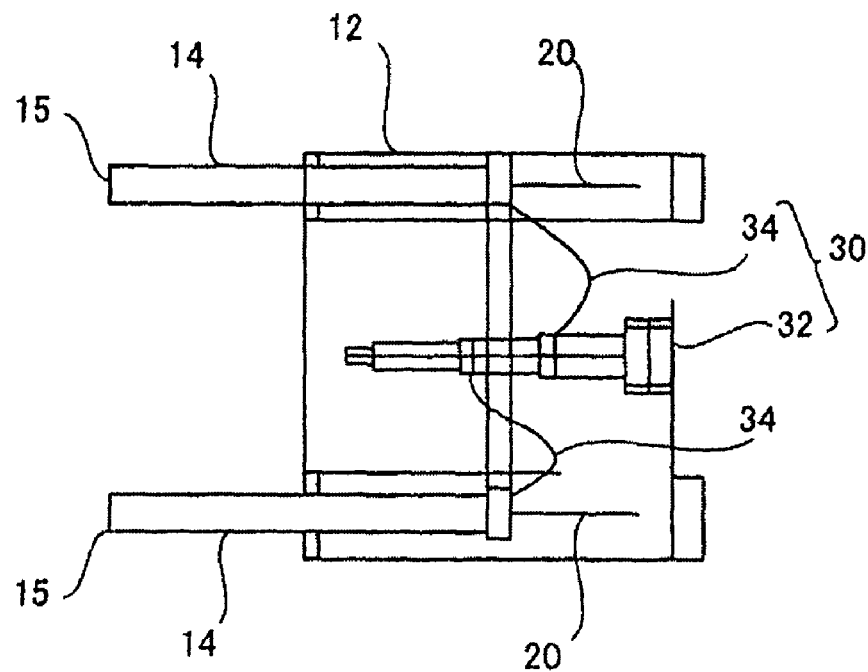
FIG. 2 is a plan view of the evoked spinal cord potential monitoring apparatus illustrated in FIG. 1.
Figure 3:
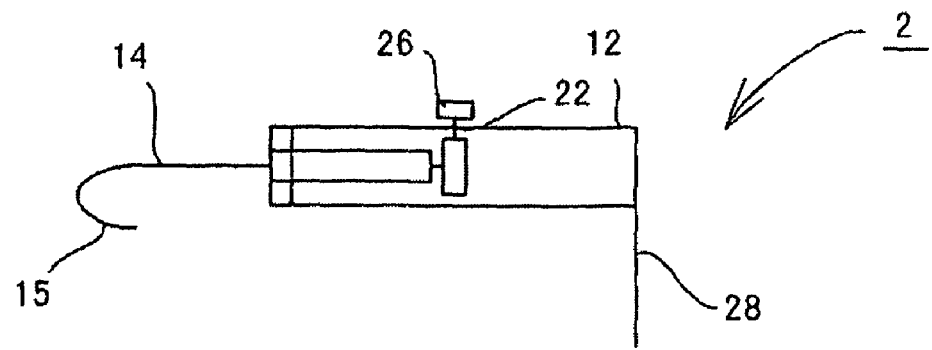
FIG. 3 is a horizontal cross sectional view of the evoked spinal cord potential monitoring apparatus illustrated in FIG. 1.
Figure 4:
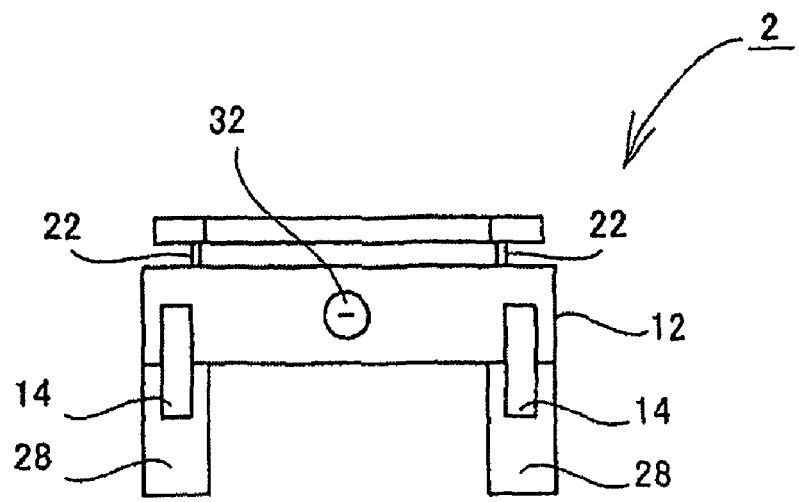
FIG. 4 is an elevation view of the evoked spinal cord potential monitoring apparatus illustrated in FIG. 1.
Figure 5:
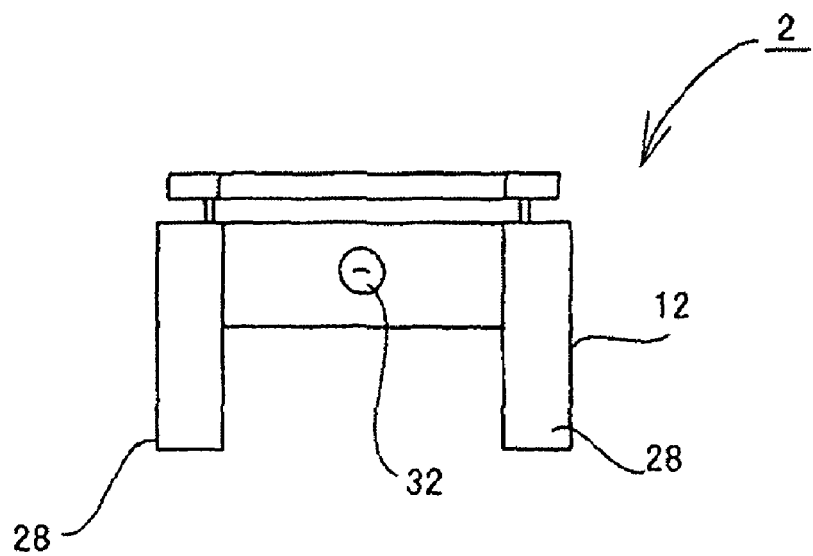
FIG. 5 is a back view of the evoked spinal cord potential monitoring apparatus illustrated in FIG. 1.

As illustrated in FIG. 2, an electrical connecting section 30 to the electrodes 14 is provided in the case 12. The upper and lower parts of the intercostal nerves of the aorta, which are intercepted during an operation, are exposed, and electrodes 14 are attached to each of the intercostal nerves. The electrical connecting section 30 is for electrically stimulating the upper intercostal nerve and for receiving the signal which is transmitted to the lower intercostal nerve through the spinal cord.

Specifically, the electrical connecting section 30 includes a stereo jack 32 positioned within the case 12; and an electrode cable 34 connected from the stereo jack 32 to the electrode 14.

An anode section of the stereo jack 32 is connected to one of the electrodes 14 on the anode side in the back end section by an electrode cable 34; and a cathode section of the stereo jack 32 is connected to the other of the electrodes 14 on the cathode side in the back end section by an electrode cable 34.

Figure 10:
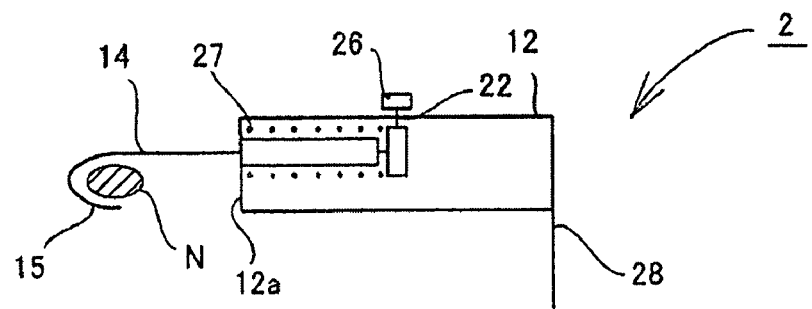
FIG. 10 is a schematic diagram of an evoked spinal cord potential monitoring apparatus according to another embodiment of the present invention.

Optionally, an elastic body 27, such as a spring, may be provided within the case 12 as a fixing section so as to bias each electrode 14 in a direction to be housed in the case 12 (FIG. 10). When the elastic body 27 is provided, the screw 26 described above may not be necessary.

When the elastic body 27 is provided within the case 12, the connecting member 24 is operated by hand to extend the electrodes 14 from the case 12, and an intercostal nerve N is coupled to the hook section 15 of each of the electrodes 14. Subsequently, the connecting member 24 is released from the hand, so that both of the electrodes 14 are moved towards the case 12 by the tensile force of the elastic body 27. The intercostal nerve N is held in between the hook section 15 and a front end surface 12a of the case 12.

For example, a coil spring may be used as the elastic body 27.

Figure 6:
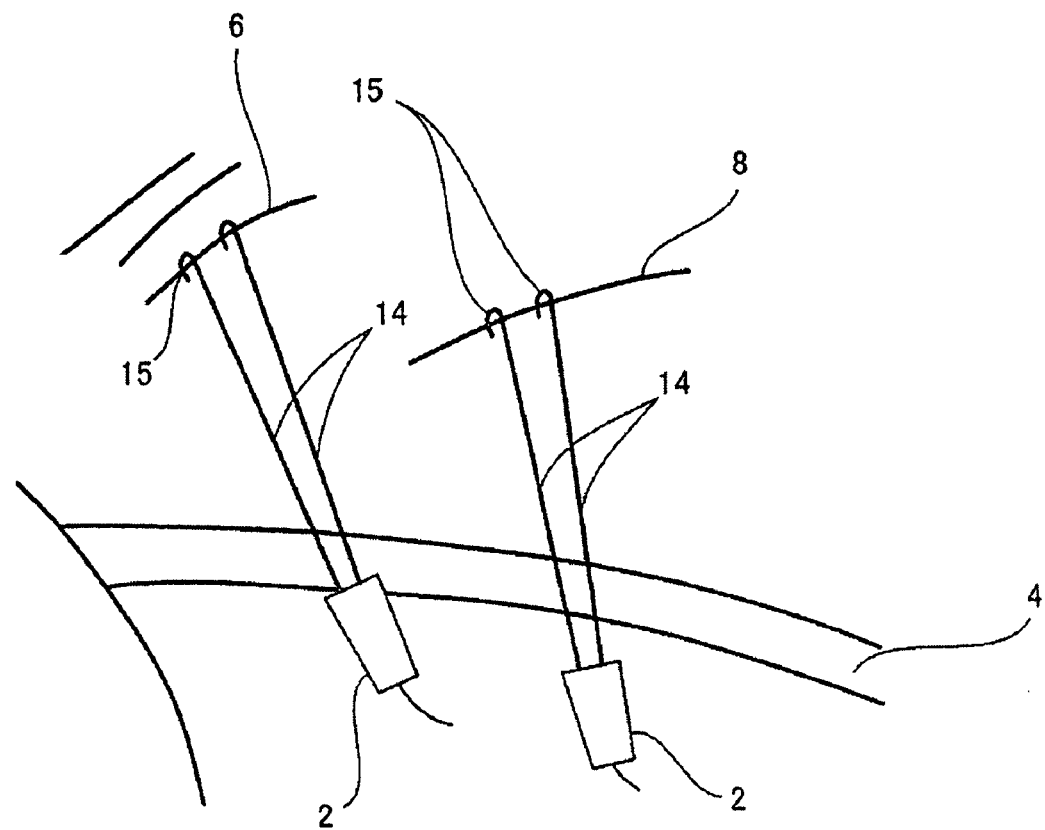
FIG. 6 is a schematic diagram illustrating a usage state of the evoked spinal cord potential monitoring apparatus according to one embodiment of the present invention.
Figure 7:
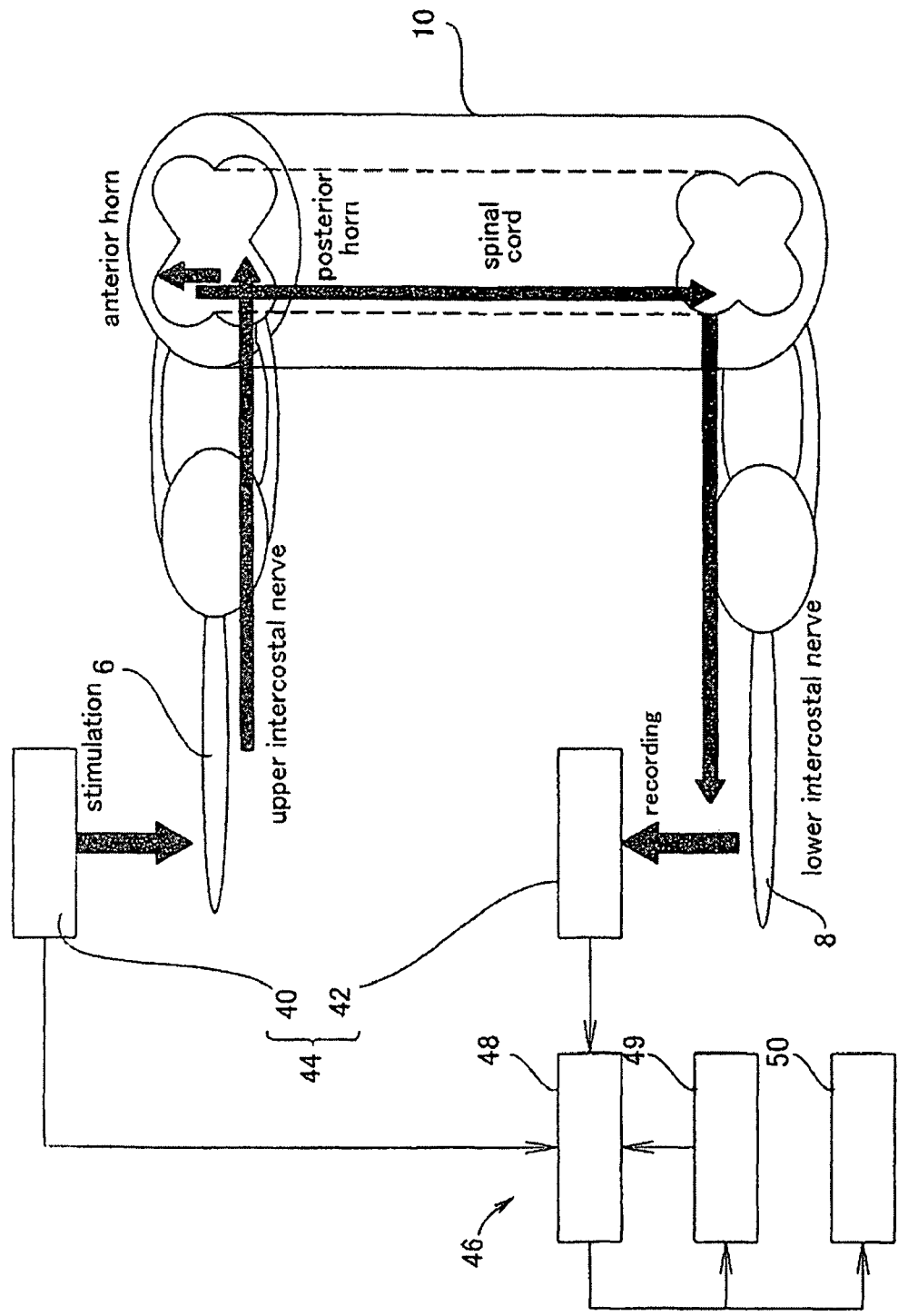
FIG. 7 is an explanatory diagram of an evoked spinal cord potential monitoring system according to one embodiment of the present invention.

As illustrated in FIGS. 6 and 7, the evoked spinal cord potential monitoring system according to the present invention includes the evoked spinal cord potential monitoring apparatus 2 with the structure described above that is attached to the exposed upper and lower intercostal nerves, and is for monitoring spinal cord ischemia during an operation. FIG. 6 is a diagram illustrating the actual utility of the potential monitoring apparatus within a dog, wherein the aorta is denoted by 4, the eleventh intercostal nerve is denoted by 6, the twelfth intercostal nerve is denoted by 8, and the spinal cord is denoted by 10.

As illustrated in FIG. 7, other than the evoked spinal cord potential monitoring apparatus 2, the evoked spinal cord potential monitoring system according to the present invention includes, as main constituent elements: a monitoring section 44 including a pulse generator 40 for generating stimulating pulses as electric stimulation applied to the spinal cord 10 and a digital oscilloscope 42 for detecting signal waveforms of evoked spinal cord potentials generated at the spinal cord 10 by the application of the stimulating pulses; and a processing section 46 for processing a monitoring result of the evoked spinal cord potentials obtained at the monitoring section 44.

The pulse generator 40 is configured to be able to output information on generated stimulating pulses to the processing section 46. A signal reading side terminal of the digital oscilloscope 42 is connected to the electrical connecting section 30 provided in the evoked spinal cord potential monitoring apparatus 2, and the digital oscilloscope 42 is configured to be able to detect signal waveforms of the evoked spinal cord potentials inputted via wirings and output the result to the processing section 46.

The processing section 46 is formed of, for example, a personal computer and the like. In this case, the processing section 46 can include: an arithmetic processing section (CPU) 48; a storing section 49 constituted of a semiconductor memory and the like; a display 50 formed of a CRT and the like. The display 50 visually displays a processing result obtained at the arithmetic processing section 48. In addition, the evoked spinal cord potential monitoring apparatus 2 may be provided with an amplifier and the like.

In order to monitor evoked spinal cord potentials, stimulating pulses (e.g., current of 10 mA or less, and 2 mA to 3 mA, in particular) are generated by the pulse generator 40, and the stimulating pulses are applied to the upper intercostal nerve 6 from the evoked spinal cord potential monitoring apparatus 2. Simultaneously, the information of the stimulating pulses is sent from the pulse generator 40 to the processing section 46. The information on the stimulating pulses inputted in the processing section 46 is provided for a process in the arithmetic processing section 48. Herein, current pulses are used as stimulating pulses; however, it is also possible to apply a voltage from the pulse generator 40 as stimulation.

Nerve cells of the intercostal nerve 6 are stimulated by the applied stimulating pulses, and as a result, evoked spinal cord potentials (evoked potential pulses) are generated in the spinal cord 10. The evoked potential pulses are propagated through a neural transmission path formed in the nerve tissues that constitute the spinal cord 10. Subsequently, electric signals are detected in the evoked spinal cord potential monitoring apparatus 2 attached to the lower intercostal nerve 8, in correspondence to the propagation of the evoked potential pulses. The detected electric signals are outputted to the digital oscilloscope 42. The digital oscilloscope 42 obtains waveforms of the evoked potential pulses as described below from the electric signals outputted from the electrodes 14.

Figure 8:
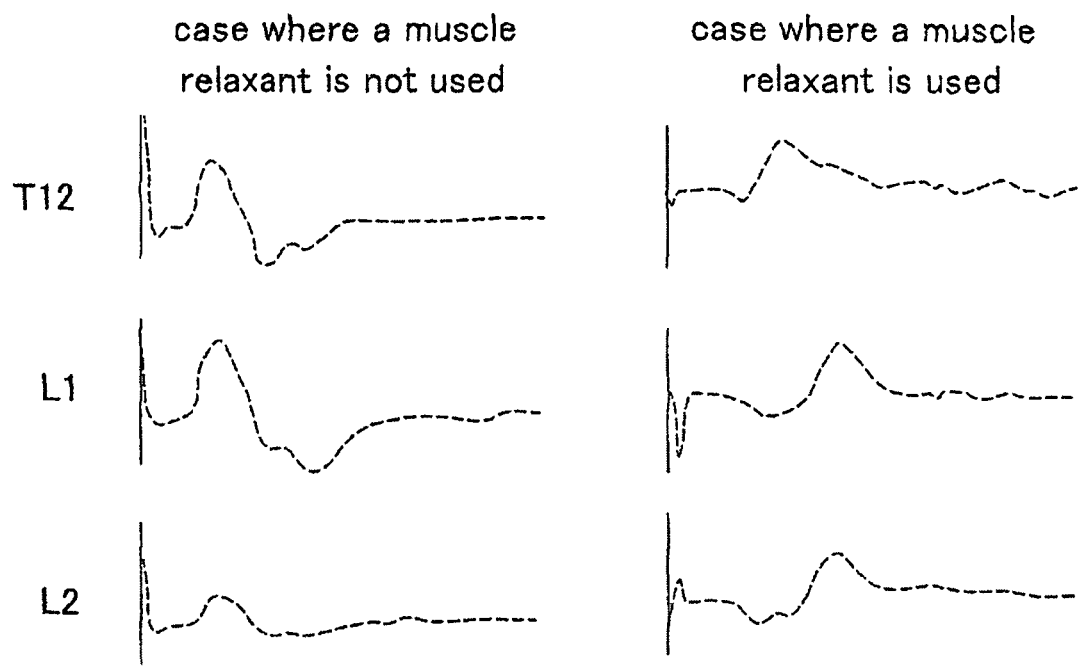
FIG. 8 is a waveform diagram obtained by using the evoked spinal cord potential monitoring system according to one embodiment of the present invention.

FIG. 8 is a diagram illustrating waveforms of evoked potential pulses obtained by the digital oscilloscope 42 based on the electric signals detected by the electrodes 14 attached to the twelfth intercostal nerve.

Herein, illustrated by stimulating pulses applied to the electrodes attached to the eleventh intercostal nerve are a waveform T12 of evoked potential pulses detected by the electrodes attached to the twelfth intercostal nerve, a waveform L1 of evoked potential pulses detected by the electrodes attached to the first lumbar nerve, and a waveform L2 of evoked potential pulses detected by the electrodes attached to the second lumbar nerve. Furthermore, it is monitored that spinal cord ischemia is not caused in the vicinity of each region of the spinal cord 10 and each region is in a normal state. If spinal cord ischemia has occurred, the pulse waveform described above will be flat.

Figure 9:
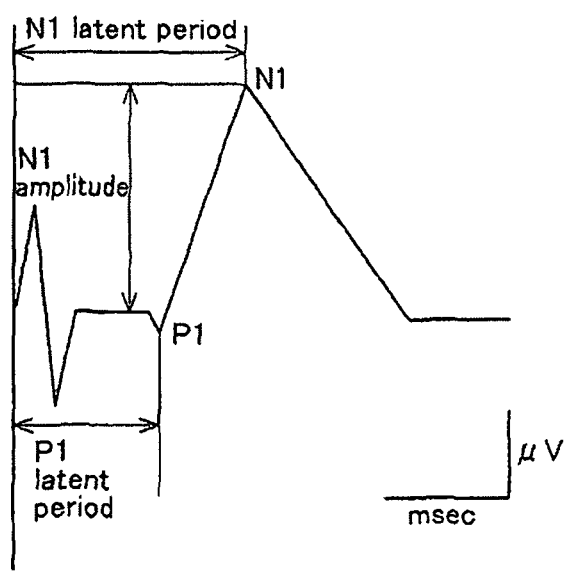
FIG. 9 is a diagram defining a waveform of a Tic-ESCP.

FIG. 8 illustrates a Tic-ESCP recorded between T12 and L2 when a muscle relaxant is applied and not applied, and the waveforms of the Tic-ESCP are formed of a small positive (P1) wave and a subsequent large negative (N1) wave in both conditions. Each of the wave and latent time is defined as illustrated in FIG. 9, and the upwards recurving in the waveform of the Tic-ESCP is defined as negative in the present invention. The waveforms were recorded more clearly from a proximal intercostal nerve than a distal one. When a muscle relaxant is applied, the small P1 wave was unclear since the N1 wave was large. The base line of the Tic-ESCP is stable and the waveform experiences few artifacts due to stimulation, so that the amplitude of the Tic-ESCP is monitored as the amplitude of the N1 wave. The latent time of the Tic-ESCP is monitored as a latent time of P1 and a latent time of N1.

The following will be apparent from the description above.

Advantages of the evoked spinal cord potential (Tic-ESCP) monitoring by the intercostal nerve stimulation include, firstly that it is unsusceptible to the influence of external noise since the waveforms of the Tic-ESCP are simple and reflect the activation along short segments of the spinal cord. Secondly, a preoperational preparation, such as placing the electrodes in the periphery of a dura mater, is not required, so that the present invention is available not only for an emergency case but also for a patient who is under an anti-blood coagulation treatment or an anti-platelet treatment. Thirdly, it can be used in conjunction with a muscle relaxant, and nerve potentials evaluated without the disturbance of the muscle. Although the electrodes are small, the waveforms are simple and clear, and therefore, it is easy to analyze the waveforms. Fourthly, stimulation is provided directly to the nerve, thus a smaller stimulation is required.

Figure 11:
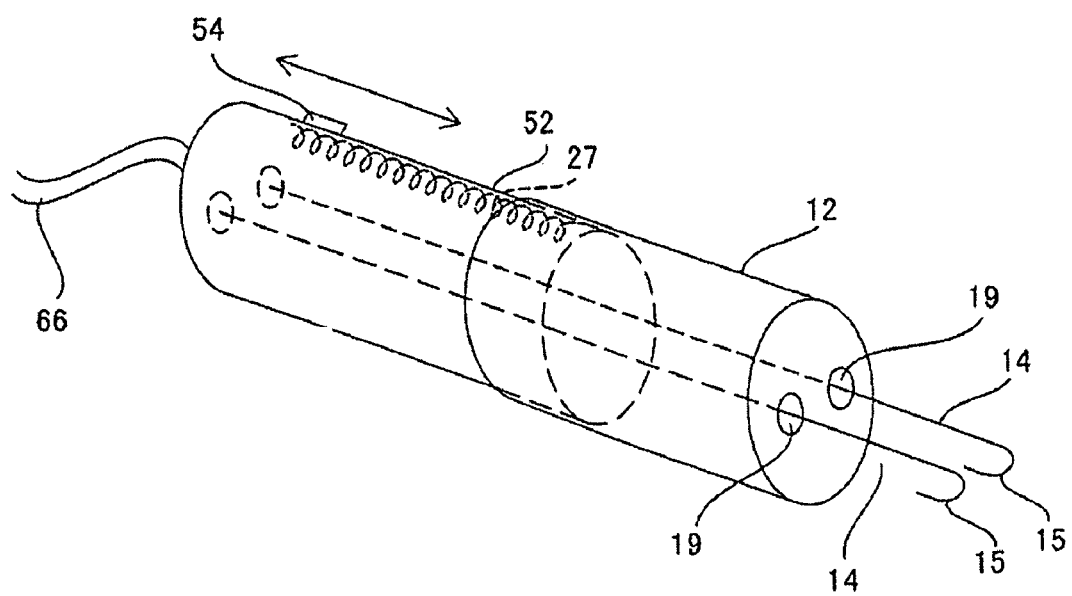
FIG. 11 is a perspective view of an evoked spinal cord potential monitoring apparatus according to another embodiment of the present invention.

FIG. 11 is a diagram illustrating another embodiment.

This embodiment includes a tubular case 12 as the holding member.

At a tip section of the case 12, an insertion aperture 19 is formed to let each of electrodes 14 through.

A pair of electrodes 14 are inserted through a tubular support section 52. A base of each of the electrodes 14 is fixed to the support section 52. The support section 52 is inserted in the case 12 to slidably move in an axis direction.

A coil spring 27 is positioned between the support section 52 and the case 12 so as to bias a hook section 15 formed at the tip of each of the electrodes 14 towards the case 12 side.

An operation projection 54 is formed on the external surface of the support section 52 so that the support section 52 or case 12 is easily operable by hand in an axis direction. An electric cord in the figure is denoted by 66.

When the operation projection 54 is operated to move the support section 52 in a longitudinal direction with respect to the case 12, the hook section 15 of each of the electrodes 14 is extended from the case 12 or moved towards the case 12.

Figure 12:
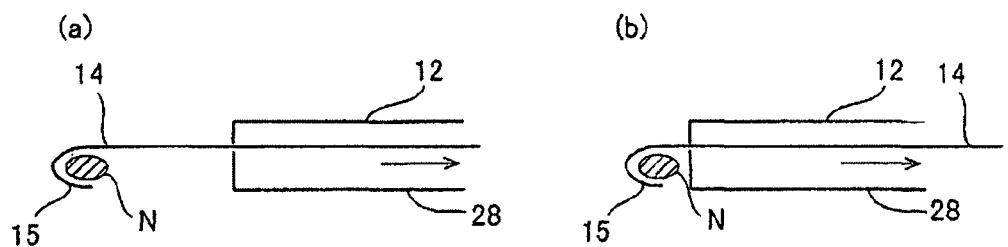
FIG. 12 is an explanatory diagram for a function of the evoked spinal cord potential monitoring apparatus illustrated in FIG. 11.

Therefore, as illustrated in FIG. 12, the intercostal nerve is coupled to the tip of the hook section 15 while the hook section 15 is extended. In the coupling state, when the operation projection is released again from hand, the support section 52 moves in the direction away from the case 12, so that the hook section 15 moves towards the case 12. As a result, an intercostal nerve N coupled to the hook section 15 is held between the tip surface of the case 12 and the hook section 15.

Figure 13:
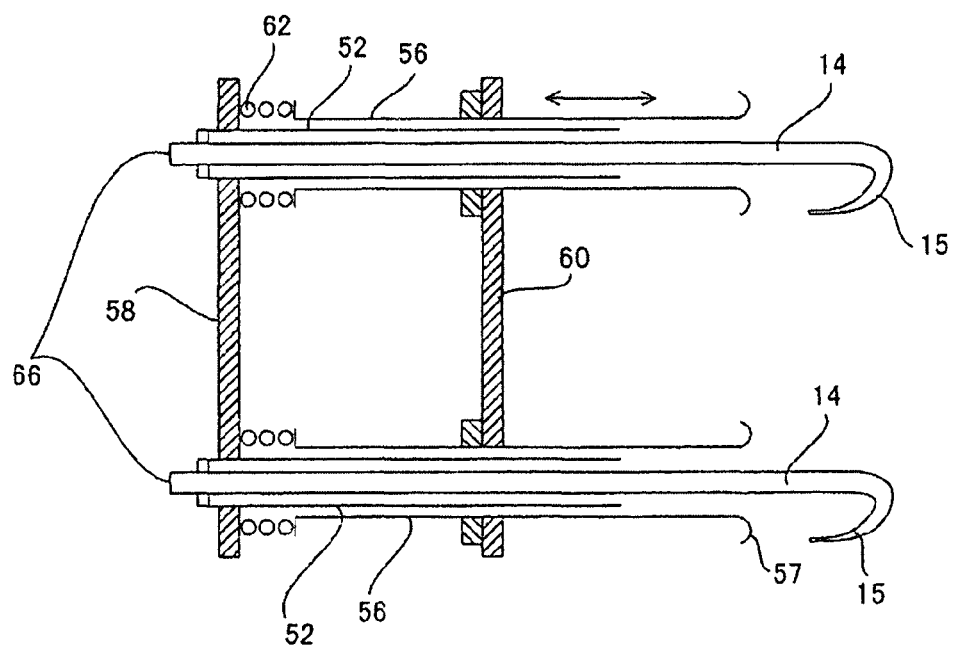
FIG. 13 is a schematic cross sectional view of an evoked spinal cord potential monitoring apparatus according to still another embodiment of the present invention.

FIG. 13 is a diagram illustrating another embodiment.

In this embodiment, an evoked spinal cord potential monitoring apparatus includes: a pair of electrodes 14; and a tube 56 as a holding section to cover each of the electrodes 14.

Each of the electrodes 14 are inserted in each of support sections 52, and the bases of the support sections 52 are connected to each other by a connecting member 58.

Each tube 56 covers each support section 52 and electrode 14 with a space therebetween, and the tube 56 is formed to be movable in an axis direction of the electrode 14. A pair of tubes 56 and 56 are connected to each other by an operation member 60.

A compressed spring 62 is provided between the base of the tube 56 and the connecting member 58 so as to bias the tube 56 in a direction separated from the connecting member 58. A flange 57 is formed at the tip section of the tube 56, the flange being extended outwards.

Therefore, when the operation member 60 is operated by hand to move the tube 56 in the direction of the connecting member 58 opposing the spring 62, a space is created between the hook section 15 of the electrode 14 and the flange 57 at the tip of the tube 56. The intercostal nerve is positioned in the space and the operation member 60 is subsequently released from the hand. As a result, the tube 56 is pushed by the spring 62 to move towards the direction of the hook section 15. The intercostal nerve is held between the hook section 15 and the flange 57.

As described above, the present invention is exemplified by the use of its preferred embodiments. However, the present invention should not be interpreted solely based on the embodiments described above. It is understood that the scope of the present invention should be interpreted solely based on the claims. It is also understood that those skilled in the art can implement equivalent scope of technology, based on the description of the present invention and common knowledge from the description of the detailed preferred embodiments of the present invention. Furthermore, it is understood that any patent, any patent application and any references cited in the present specification should be incorporated by reference in the present specification in the same manner as the contents are specifically described therein.

The invention claimed is:

1. An evoked spinal cord potential monitoring system for monitoring spinal cord ischemia during an operation, comprising evoked spinal cord potential monitoring apparatuses attached respectively to an exposed upper intercostal nerve and an exposed lower intercostal nerves,
   wherein:
   each of the evoked spinal cord potential monitoring apparatuses includes a pair of electrodes; and a holding section for holding the pair of electrodes, a tip section of each of the electrodes being extended outwards from an end of the holding section, and the electrodes being movable relative to the holding section; and
   a hook section engageable to the exposed upper intercostal nerve or the exposed lower intercostal nerve is provided at the tip section of each of the electrodes, the hook section is engaged to the intercostal nerve such that the hook section and the holding section are able to hold the intercostal nerve therebetween
   wherein the evoked spinal cord potential monitoring apparatus configured to be attached to the exposed upper intercostal nerve includes an electric stimulation section, and the evoked spinal cord potential monitoring apparatus configured to be attached to the exposed lower intercostal nerve includes a recording section for recording electric signals conducted from the spinal cord to the lower intercostal nerve as waveforms, wherein the electric stimulation section comprises a pulse generator and the recording section comprises a digital oscilloscope and a processing section wherein the holding section includes therein an electric connection section to the electrodes wherein the electric connection section includes: a stereo jack, and an electrode cable for connecting the stereo jack and the electrodes and wherein the recording section records trans-intercostal evoked spinal cord potentials.

2. An evoked spinal cord potential monitoring system according to claim 1, wherein:

The holding section is a case, and the pair of the electrodes are positioned in the case such that the pair of the electrodes are extendable out of and retractable in the case;

a spring is provided between each of the electrodes and the case to retract the pair of electrodes in the case; and the hook sections of the electrodes and a tip section of the holding section are able to hold the intercostal nerve therebetween.

3. An evoked spinal cord potential monitoring system for monitoring spinal cord ischemia, comprising evoked spinal cord potential monitoring apparatuses attached respectively to an exposed upper intercostal nerve and an exposed lower intercostal nerves of an aorta intercepted during an operation, wherein:

each of the evoked spinal cord potential monitoring apparatuses includes a pair of electrodes; and a holding section for holding the pair of electrodes, a tip section of each of the electrodes being extended outwards from an end of the holding section, and the electrodes being movable relative to the holding section; and a hook section engageable to the exposed upper intercostal nerve or the exposed lower intercostal nerve is provided at the tip section of each of the electrodes, and the electrodes or the holding section is moved while the hook section is coupled to the intercostal nerve such that the hook section and the holding section are able to hold the intercostal nerve therebetween wherein the evoked spinal cord potential monitoring apparatus configured to be attached to the exposed upper intercostal nerve includes an electric stimulation section, and the evoked spinal cord potential monitoring apparatus configured to be attached to the exposed lower intercostal nerve includes a recording section for recording electric signals conducted from the spinal cord to the lower intercostal nerve as waveforms, wherein the electric stimulation section comprises a pulse generator and the recording section comprises a digital oscilloscope and a processing section wherein the holding section includes therein an electric connection section to the electrodes wherein the electric connection section includes: a stereo jack, and an electrode cable for connecting the stereo jack and the electrodes and wherein the recording section records trans-intercostal evoked spinal cord potentials.

4. The evoked spinal cord potential monitoring system according to claim 1, wherein the holding section includes a fixed prong which is thrustable into tissues.

5. The evoked spinal cord potential monitoring system according to claim 1, wherein a space between the pairs of the electrodes is 2 to 3 mm.

6. The evoked spinal cord potential monitoring system according to claim 3, wherein the holding section includes a fixed prong which is thrustable into tissues.

* * * * *